(12) United States Patent
Alexandrov et al.

(10) Patent No.: US 10,752,872 B2
(45) Date of Patent: Aug. 25, 2020

(54) SYSTEM AND METHOD FOR AUTOMATED EXTRACTION OF MULTI-CELLULAR PHYSIOLOGICAL PARAMETERS

(75) Inventors: Yuriy Alexandrov, Cardiff (GB); Albert Francis Santos, Cardiff (GB)

(73) Assignee: GE Healthcare UK Limited, Little Chalfont (GB)

( * ) Notice: Subject to any disclaimer, the term of this patent is extended or adjusted under 35 U.S.C. 154(b) by 309 days.

(21) Appl. No.: 13/634,613

(22) PCT Filed: Mar. 18, 2011

(86) PCT No.: PCT/EP2011/054103
§ 371 (c)(1),
(2), (4) Date: Sep. 13, 2012

(87) PCT Pub. No.: WO2011/113924
PCT Pub. Date: Sep. 22, 2011

(65) Prior Publication Data
US 2013/0004938 A1 Jan. 3, 2013

(30) Foreign Application Priority Data
Mar. 19, 2010 (GB) .................................. 1004614.2

(51) Int. Cl.
*C12M 1/36* (2006.01)
*C12M 3/00* (2006.01)

(52) U.S. Cl.
CPC ............ *C12M 41/48* (2013.01); *C12M 21/08* (2013.01)

(58) Field of Classification Search
None
See application file for complete search history.

(56) References Cited

U.S. PATENT DOCUMENTS

| | | | |
|---|---|---|---|
| 4,154,652 A | 5/1979 | Sawamura et al. | |
| 6,197,575 B1 * | 3/2001 | Griffith | B01J 19/0046 435/288.4 |
| 7,270,996 B2 * | 9/2007 | Cannon | C12M 23/42 435/286.5 |
| 7,348,175 B2 * | 3/2008 | Vilendrer et al. | 435/284.1 |
| 2008/0070304 A1 * | 3/2008 | Forgacs | C12N 5/0062 435/397 |
| 2009/0075360 A1 * | 3/2009 | Ho et al. | 435/284.1 |

FOREIGN PATENT DOCUMENTS

| | | |
|---|---|---|
| DE | 102005021034 | 11/2006 |
| WO | 9947922 A | 9/1999 |
| WO | 03087292 A2 | 10/2003 |
| WO | 2005116186 A1 | 12/2005 |
| WO | WO 2006/060214 | 6/2006 |
| WO | WO 2009/107915 | 9/2009 |
| WO | WO 2010/022391 | 2/2010 |

OTHER PUBLICATIONS

Oh SKW, et al., Long-term Microcarrier Suspension Cultures of Human Embryonic Stem Cells, Stem Cell Research 2:219-230, 2009.*
Puskeiler et al., Miniature Bioreactors for Automated High-throughput Bioprocess Design (HTBD): Reproducibility of Parallel Fed-Batch Cultivations with *Escherichia coli*, Biotechnol. Appl. Biochem 42:227-235, 2005.*
Grande et al., Evaluation of matrix scaffolds for tissue engineering of articular cartilage grafts, Journal of Biomedical Materials 34(2), 211-220, 1997.*
Martin et al., The Role of Bioreactors in Tissue Engineering, Trends in Biotechnology, 22(2):80-86, 2004.*
Henson, Dynamic modeling and control of yeast cell populations in continuous biochemical reactors, Computers and Chemical Engineering 27, 1185-1199, 2003.*
Cherry et al., Hydrodynamic effects on cells in agitated tissue culture reactors, Bioprocess engineering 1 (1986), 29-41.*
GE Healthcare, IN Cell Analyzer 2000, pp. 1-12, retrieved from http://www.ebiotrade.com/custom/GE/110525tw/images/A1.pdf on Dec. 16, 2014.*
Placzek, M., et al., Journal of the Royal Society Interface, vol. 6, No. 32 (2009) 209-232.
Takahashi, K., et al., Cell, vol. 131, No. 5 (2007) 861-872.
Search Report and Opinion issued in connection with related GB Application No. 1004614.2 dated Jul. 19, 2010.

* cited by examiner

*Primary Examiner* — Andrea S Grossman
(74) *Attorney, Agent, or Firm* — Eversheds Sutherland (US) LLP (57) ABSTRACT

In one aspect the present invention relates to a system 100 for automated extraction of multi-cellular physiological parameters. The system 100 comprises a morphogenesis module 160 for growing a plurality of cells, a monitoring unit 110 for monitoring the plurality of cells, a controller 140 for controlling the morphogenesis module 160 and the monitoring unit 110 to grow the plurality of cells and analyse the growth of the plurality of cells in order to determine the multi-cellular physiological parameters, the controller (140) further comprising a process modelling unit (146) for determining inter-cellular interactions in response to various process conditions. The multi-cellular physiological parameters may provide an optimised protocol for growing various tissue types. A further aspect of the present invention provides a method 200 for automated extraction of multi-cellular physiological parameters. The method 200 comprises growing 202 a plurality of cells, monitoring 204 the plurality of cells, and analysing 206 the growth of the plurality of cells in order to determine 208 the multi-cellular physiological parameters, and adaptively modifying a process model to provide a learning algorithm for determining an optimised tissue growth protocol. The cells may, for example, include pluripotent stem cells, or derived differentiated cells.

6 Claims, 7 Drawing Sheets

FIG. 1

FIG. 2 ditch 1: Cycle=11 Time=10.000 dt=1.1475 p2 Nodes=8380 Cells=4153 RMS En=3.9e-4
integral= 2177.038 ditch 1: Cycle=28 Time=10.000 dt=1.2341 p2 Nodes=5551 Cells=2742 RMS En=4.3e-4
integral= 1929.528

SYSTEM AND METHOD FOR AUTOMATED EXTRACTION OF MULTI-CELLULAR PHYSIOLOGICAL PARAMETERS

CROSS-REFERENCE TO RELATED APPLICATIONS

This application is a filing under 35 U.S.C. 371 of international application number PCT/EP2011/054103, filed Mar. 18, 2011, published on Sep. 22, 2011 as WO 2011/113924, which claims priority to application number 1004614.2 filed in Great Britain on Mar. 19, 2010.

FIELD

The present invention relates generally to a system and method for automated extraction of multi-cellular physiological parameters from living cells grown in culture. More particularly, the present invention relates to a method and system that can be used to automatically determine at least one step for an optimised cell and tissue growth protocol.

BACKGROUND

A great deal of research effort has been directed in recent years to understanding how mammalian cells develop in order to form complex structures (for example, tissue) from multi-cellular aggregations. Indeed, various high-throughput screening (HTS) robotic systems [1, 2] have been used to help identify potentially significant factors controlling how cell growth, motility, programmed cell death and epigenetics, for example, lead to the growth of such complex tissue structures. However, these latter HTS systems often rely on manual intervention in order to interpret datasets from a series of inputs. Such inputs can include, but are not limited to, optical images of cells obtained from microscopes or equivalent automated image capture instruments. Other inputs can also include 1) electrophysiological data from cells and 2) analysis of content of biological molecules which are present either on the surface of the cells, or contained within the cell. In many instances, the speed of resolution of these systems may not be appropriate for observation of relatively rapid temporal changes that may be of significance in the tissue growth and development process.

Such research also impacts upon the potential use of pluripotent stem cells for the generation and survival of such tissue structures [3, 4, 5], for example, for wound-healing or tissue replacement, therapy. However, whilst much research effort is being directed to the use of stem cells for tissue regeneration, the overall process that is necessary for successful tissue growth of tissue structures, such as whole skin epithelium, cartilage and organs, is still not well-understood. For example, inter-cellular interactions are complex, and it is thus experimentally difficult to determine optimal conditions for growing certain specific types of tissue. This is due to the large number of chemical and biological factors involved. In addition, there is an influence from variable environmental and physical conditions that might be present (such as temperature, pressure, humidity, $O_2/CO_2$ levels, light illumination levels etc. as well as the topography and surface properties of any cellular support matrices that may be present).

Accordingly, the present invention has been devised whilst bearing the above-mentioned drawbacks associated with conventional techniques in mind.

SUMMARY

According to a first aspect of the present invention, there is provided a system for automated extraction of multi-cellular physiological parameters. Various embodiments of the present invention comprise a morphogenesis ("shape-forming") module for growing a plurality of cells, a monitoring unit for monitoring the plurality of cells, a controller for controlling the morphogenesis module and the monitoring unit to grow the plurality of cells, the controller further comprising a process modelling unit for determining inter-cellular interactions in response to various process conditions. The controller is also configured to analyse the growth of the plurality of cells in order to determine the multi-cellular physiological parameters. Such multi-cellular physiological parameters may, for example, define one or more protocol steps for producing a specific tissue type.

According to a second aspect of the present invention, there is provided a method for automated extraction of multi-cellular physiological parameters. The method comprises growing a plurality of cells, monitoring the plurality of cells, analysing the growth of the plurality of cells in order to determine the multi-cellular physiological parameters, and adaptively modifying a process model to provide a learning algorithm for determining an optimised tissue growth protocol.

Various aspects and embodiments of the present invention enable rapid automated screening of multiple morphogenesis phenomena with many cell precursors against many extra-cellular matrix (ECM) media, chemical signalling agents, physical and chemical conditions, morphogens, ligands (drugs), etc. They also permit characterisation of morphogenesis in terms of underlying physical and physiological mechanisms, as well as enabling the possibility of developing specialised (pre-programmed) courses of morphogenesis to create specific tissue types.

BRIEF DESCRIPTION OF THE DRAWINGS

Various aspects and embodiments of the present invention will now be described in connection with the accompanying drawings, in which.

DETAILED DESCRIPTION

Figure 1:
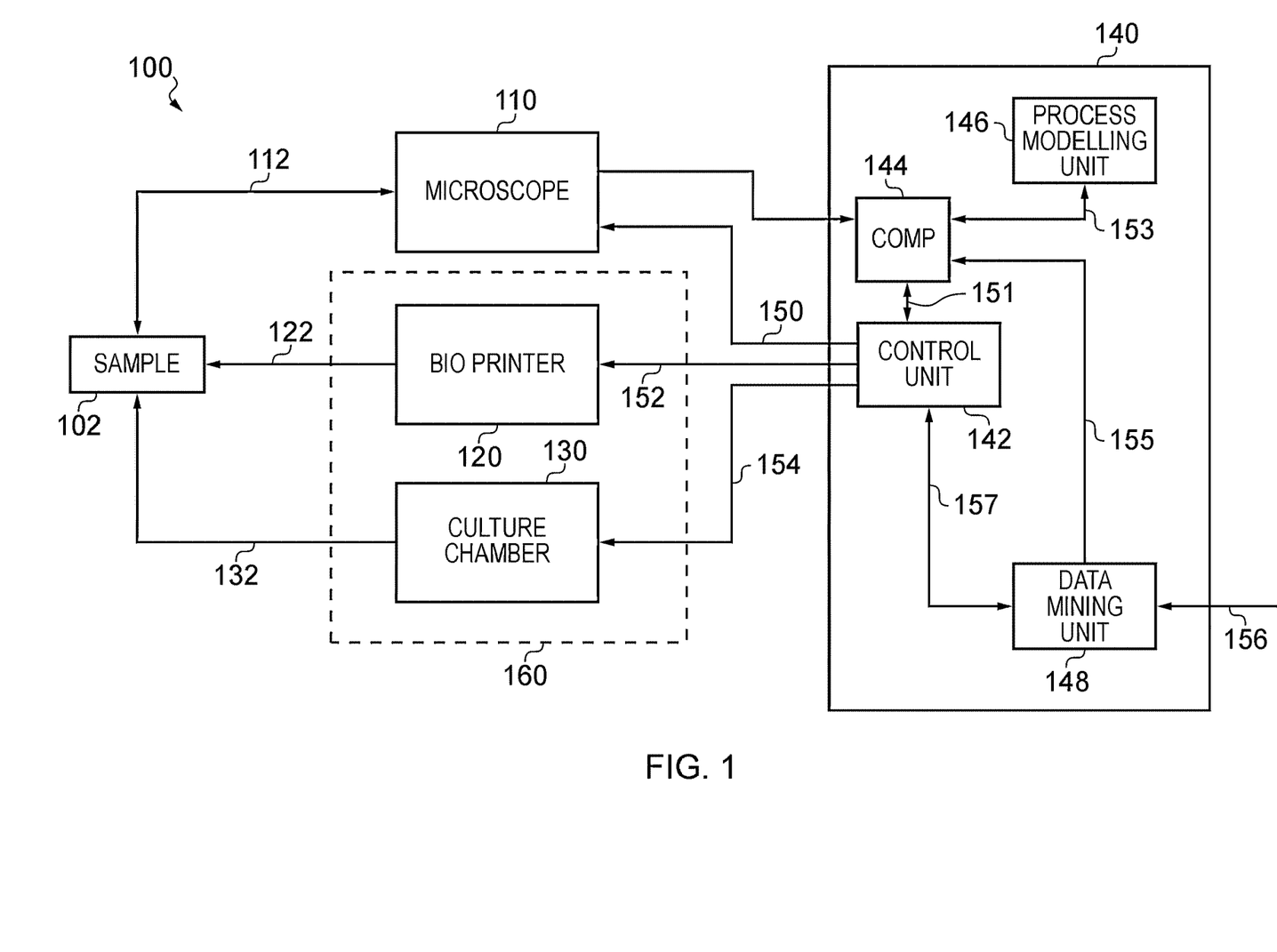
FIG. 1 shows a system for automatic extraction of multi-cellular physiological parameters in accordance with an embodiment of the present invention.

FIG. 1 shows a system 100 for automatic extraction of multi-cellular physiological parameters. Such multi-cellular physiological parameters may, for example, be used to define a protocol of one or more sequentially applied steps necessary to grow a (complex) tissue sample and/or various protocol parameters used in such protocol steps. Protocol parameters might include, for example, one or more of: pH, temperature, pressure, humidity, $O_2/CO_2$ levels, illumination levels, illumination wavelength, agents/reagents, ECM media, chemical signalling agents, physical and chemical conditions, morphogens, ligands, drugs, etc.

The system 100 includes a morphogenesis module 160 for growing a plurality of cells. For example, the morphogenesis module 160 is a device that can make or grow a multi-cellular tissue sample 102. In the embodiment of FIG. 1, the morphogenesis module 160 includes a bio-printer 120 and a culture chamber 130. However, in various embodiments the morphogenesis module 160 may include, for example, a stem cell based tissue growth unit and/or an extra-cellular matrix (ECM) provider (not shown). For example, an ECM may be provided by an ECM gel such as PURAMATRIX available from 3DM, Inc. of Cambridge, Mass., USA.

Various commercially available incubator chambers are able to control $CO_2$, temperature, oxygen levels, pH and humidity. Such environmental control is important for studying engineered tissue constructs (ETC's) and for implementing programmed courses of morphogenesis aimed at the synthesis of different specialised tissues, such as, for example, neuronal, muscular and bone tissues.

In various embodiments, an incubator chamber is operable to store a multitude of "printouts" in separate hermetic slots, whilst maintaining individual environmental conditions for each sample through common process control software. The same control unit is able to run an extraction of a printout from an incubator and move it back to the bio-printer (e.g. for further deposition of cell layers, ECM gels and/or drugs/morphogens/fluors/etc.) or a microscope specimen stage (e.g. if structural examination is needed).

A process control unit may be provided that uses scheduling algorithms to enable the parallel implementation of various different protocols, avoiding interference between samples. Such a design permits the assessment of process/ protocol viability, speed and outcome in real time, which thus enables determination of optimised protocols for various industrial applications.

In various embodiments, a single-(field-of-view) FOV sample with deposited ETC is mounted in a frame or holder having a size of a few millimetres and moved by a ribbon conveyor or the like. In other embodiments, a larger sample may be derived from a well plate and adapted for bio-printing. For example, bio-printing may use commercially available devices from companies such as Sciperio of 6421 S. Air Depot Blvd., Suite B, Oklahoma City, Okla. 73135, USA.

A monitoring unit 110 is also provided in the system 100 for monitoring the plurality of cells. In this embodiment, the monitoring unit 110 includes a HTS microscope, such as an IN Cell Analyzer 2000 system commercially available from GE Healthcare, Amersham, UK, for providing automated feedback regarding the growth state of the plurality of cells forming the sample 102. Such a HTS microscope can be used to scan multiple cell samples to provide data that can then be used to screen for the effects of various combinations of protocol parameters.

The system 100 further includes a controller 140 for controlling the morphogenesis module 160 and the monitoring unit 110 to grow the plurality of cells and analyse the growth of the plurality of cells in order to determine the multi-cellular physiological parameters. The controller 140 may be provided by a selection from a number of several hardware, software and/or firmware modules. In one embodiment, the controller 140 can be provided by an appropriately programmed computer connected to an IN Cell Analyzer 2000 device provided in the monitoring unit 110.

The controller 140 includes a control unit 142 which can generate multi-component data for multi-component analysis from data provided by the monitoring unit 110. The control unit 142 is connected to the bio-printer 120 via control line 152 and to the culture chamber 130 via control line 154. Additionally, control unit 142 controls the monitoring unit 110 via control bus 150. In various embodiments, the control unit 142 provides large-scale parallel processing to automatically identify tissue engineering workflow, or at least a part thereof.

A comparator 144, provided in the controller 140, is connected to the monitoring unit 110 and the control unit 142 through data line 151. The comparator unit 144 can provide part of a feedback loop for optimising a match between desired inter-cellular interactions and process conditions to determine an optimised protocol step in a tissue growth process.

The controller 140 further comprises a process modelling unit 146 connected to the comparator 144 through data line 153, and a data mining unit 148 connected to the comparator 144 through data line 155 and to the control unit through data line 157. An external data feed 156 is also provided to the data mining unit 148. The data mining unit 148 can be used for acquiring test protocol steps from an external information source. The data mining unit 148 may operate using service software that standardises the data format of any data that is retrieved. The process modelling unit 146 may, for example, be used to determine inter-cellular interactions in response to various process conditions. Various embodiments of the present invention, may, for example, incorporate one or more commercially available software modules such as: Compucell3D, JDesigner, VCell, or MAYA.

In various embodiments the process modelling unit 146 applies various non-linear physics, self-organisation and morphogenesis theories. These may include theories for symmetry breaking and topological instability, anisotropic aggregation, organ size conservation in polyploids, allometry, cell differentiation, cell proliferation, germ/soma separation in the course of evolution, wound healing, embryo development, etc.

In operation the bio-printer 120 is used to print cells, having one or more phenotypes that are grown in the culture chamber 130, and can include a tissue sample 102, which may be two- or three-dimensional. Such cells can be printed layer by layer onto an ECM to build up the tissue sample 102. Progress in the evolution of the tissue sample 102 can be monitored by the controller 140 from a plurality of images of the sample acquired by the monitoring unit 110. Such images may be multi-channel images provided by imaging the sample 102 at various different wavelengths and/or a sequence of images acquired over various time periods. One advantage of the system 100 is that such time periods may be relatively short (e.g. on a timescale period of about 1 millisecond, 10 milliseconds, 100 milliseconds, 1 second, 10 seconds or 100 seconds). This enables the system 100 to monitor relatively rapid changes in the sample 102 to find potentially significant physiological parameters that cannot readily be obtained using conventional systems.

The process modelling unit 146 is operable to generate one or more hypothetical protocols for growing the tissue sample 102. These are tested by the comparator 144 against both actual tissue growth results determined by the monitoring unit 110 and theoretical hypotheses provided by the data mining unit 148. By enabling the system 100 to import hypotheses from external data sources, controller 140 adaptively applies an optimisation algorithm that identifies the most probable sequence of multi-cellular physiological parameters defining protocol steps necessary to grow the tissue sample 102. An example of such an algorithm is described in greater detail below, in connection with FIG. 2.

The system 100 is thus adapted to automatically apply the most up to date research theorems to identify optimal conditions for growing specific useful tissues/structures, having a particular desired phenotype. Such a system can thus be totally automated and/or used as a research tool that automatically identifies at least one protocol step and its/their associated parameters.

For example, the system 100 can help identify optimal cell types, ECM gel, morphogens, ligands, reagent(s), time periods, temperatures, illumination level(s), pressure, atmosphere ($N_2/CO_2/O_2$/etc. levels), sequence of application, concentration, cell child-to-parent ratio, etc., when studying and/or directing cell-cell and cell-ECM interactions in controlled environments.

In various embodiments, the morphogenesis module 160 is further operable to provide an extra-cellular matrix (ECM) on which the plurality of cells are grown. The ECM and the plurality of cells may together provide the tissue sample 102.

Figure 2:
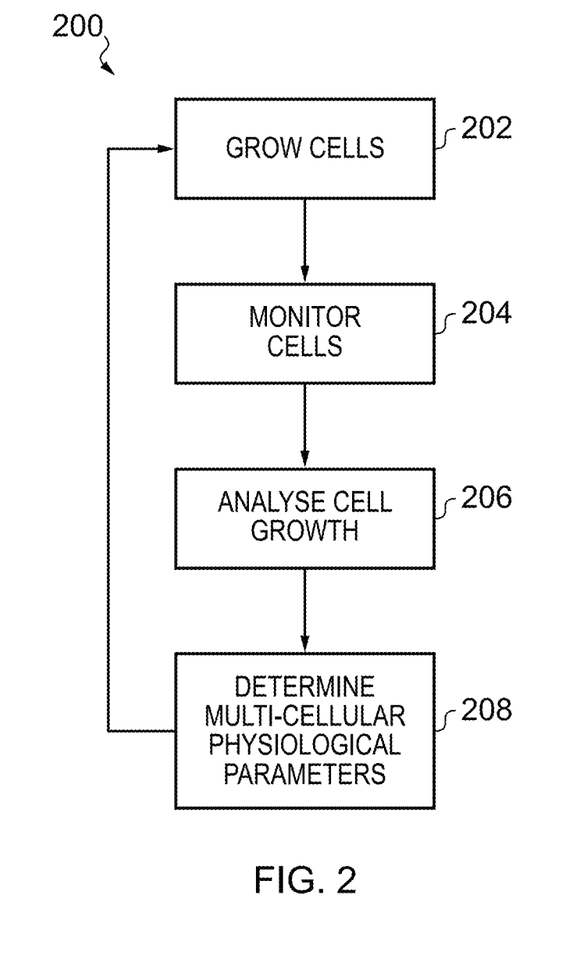
FIG. 2 shows a method for automatic extraction of multi-cellular physiological parameters in accordance with various embodiments of the present invention.

FIG. 2 shows a method 200 for automatic extraction of multi-cellular physiological parameters in accordance with various embodiments of the present invention. The method 200 may, for example, be implemented using a system such as the system 100 depicted in FIG. 1.

The method 200 includes a first step 202 of growing a plurality of cells. Once grown, a second step 204 of the method 200 is to monitor the plurality of cells. Having monitored the cells for a desired duration, the method 200 uses a third step 206 to analyse the growth of the plurality of cells. Finally, a fourth step 208 of determining the multi-cellular physiological parameters from the results of analysis step 206 is applied.

The method 200 may repeat many times in order to analyse the growth of the cells and, for example, their response to various chemical, physical and/or biological conditions.

Continual application of the method 200 enables an adaptive learning algorithm to be applied in order to determine a set of morphogenesis protocols for engineering a specific tissue type from the multi-cellular physiological parameters. For example, the cells may be stem cells and the multi-cellular physiological parameters define one or more factors that are necessary to induce pluri-potency in the stem cells.

The step 202 of growing the cells may include providing an extra-cellular matrix (ECM) on which the plurality of cells are grown. For example, an ECM may initially itself be grown before applying various cell(s), cell precursors, etc., that create the plurality of cells for forming a tissue sample. Alternatively, various commercially available ECM's, such as PURAMATRIX may be used.

In various embodiments, a collagen type I hydrogel in a 3D close packed grid-like geometry is provided. This can be overlaid by bio-printing of cell layers to build up a tissue sample. The action of various chemical cues can be monitored during such a build up process to determine which factors or protocols affect growth parameters such as angiogenesis, for example. Such chemical cues may include, for example, immune camouflage agents, signalling molecules, morphogens, chemoattractants, cytokines, motifs, antibodies, neurotransmitters and hormones.

The step 204 of monitoring the cells may use a robotised optical microscope, working with fluorescent and/or brightfield modality covering a size range from about 0.4 μm to about $2 \times 10^3$ μm, with cell-size resolution and a large field-of-view (FOV). Cooperative inter-cellular effects essential for morphogenesis and for incipient organogenesis usually involve cell numbers in the range from about $10^2$ to about $10^5$. Given that in further stages of tissue development, larger tissue samples are formed by scaling and/or repeat mechanisms, imaging of tissue structures at a scale larger than about 2 mm is unlikely to be needed. Images of the tissue sample may be acquired from the live cell cultures over a physiological time period, such as, for example, from about 1 second to about $10^5$ seconds.

The step 206 of analysing the growth of the plurality of cells may include comparing the monitored cells to one or more morphogenesis models for determining inter-cellular interactions in response to various process conditions. Microscopy and image analysis may be applied to segment single cells, cell aggregates and tissue structures in 2D and/or 3D. Corresponding sets of structural descriptors for segmented objects are developed in order to compare geometry of the grown tissue sample 102 with theory. These descriptors include, for example, object density, orientation and mutual location of cells and cellular aggregates.

In analysing the tissue sample growth, mapping of the actual sample to the geometrical model space may be performed. In various embodiments, this entails provision of special fiducial marks on the sample, subsequent recognition of these marks and the binding of geometric data.

Various approaches can be taken for modelling morphogenesis in multi-cellular systems, and certain embodiments of the present invention can use any one or a combination of the following described approaches:

1) The model may be generated using ordinary differential equations (ODE). The ODE approach ignores or oversimplifies spatial effects, but may be used as an auxiliary tool in assessing the dynamics of overall cell numbers in cellular populations.

2) The model may be generated using partial differential equations (PDE). The PDE approach may use cell density in a diffusion or hydrodynamics approximation. The validity of the hydrodynamics approach is supported by experimental evidence of tissue fluidity. Morphogen dynamics can be treated by using the diffusion approximation. Technically, PDE models are quite complex and numerical solution time consuming. Various known models exist, which are generally constructed for 2D space. In the case of angiogenesis, the system characterisation was obtained by analysing and adjusting the following parameters: a) morphogen diffusion coefficient; b) cell "diffusion coefficient"; c) cell chemotactic sensitivity; d) cell traction coefficient; e) morphogen production rate; f) morphogen decay rate; and g) cell "rigidity". Various PDE models of angiogenesis may also take into account stress/deformation fields coupled with cell distribution and/or more complex effects of cell population interactions.

3) The model may be generated using cell automata (CA), which is also known as the cellular Potts model (CPM). The CA approach distinguishes the behaviour of single cells, representing the sample in a lattice approximation. CA models may be used to model cell aggregation, which whilst computationally expensive, provides considerable flexibility, describing the sample in terms of cell-cell and cell-ECM bond energies (governing contact inhibition), cell resistance to compression and elongation, and chemotactic sensitivity. The morphogen dynamics may be governed by a built-in PDE as per that used in the PDE approach. CA models can be used for both 2D and 3D samples. Some may be tuned by segmenting the sample space according to physiological function, e.g. into "far", "sorting" ("apical"), and "frozen" zones depending upon the prevalent regime of cellular activity.

4) The model may be generated using stochastic differential equations (SDE). The SDE approach has been applied for analysing cell motility data. The automated image analysis technique needed for SDE ("cell tracking") gathers coordinate information for many individual cells over a specified time period. SDE theory provides relatively simple theoretical expressions that can then be fitted to experimental data. At least three parameters of cell motility can be derived from the fit: i.e. the mean square velocity, the directionality and the persistence time (namely the time that cells grow in a specific direction before changing their growth direction). SDE theory explains oscillatory anomalies in the measured mean square displacements, an effect that is well known from experiment.

Various other cell effects may also be taken into account in the ODE, PDE and CA/CPM models, such as, for example, cell sorting/differentiation, proliferation and cell death.

In one preferred embodiment, PDE and CA modelling is used to simulate the 2D or 3D physical space of the sample. The combined model defines interactions that are essential to morphogenesis and which can thus test theory against measured sample parameters to obtain the multi-cellular physiological parameters.

The step 208 of determining the multi-cellular physiological parameters in a preferred embodiment entails comparing the output of the combined PDE and CA model to either 2D or 3D images obtained of the sample, for example by using a conventional two-point correlation technique [6].

Both the model and the imaging system used to image the tissue sample are set to image a sample having a maximum size of 2×2×2 mm (in 3D) or 2×2 mm (in 2D) with a simulation and imaging resolution set to be 5 µm. Such simulations involve a maximum of about $1.6 \times 10^6$ lattice nodes for CA modelling, which is not unreasonable from a computational resources point of view.

Step 208 can be applied by using large-scale parallel processing to automatically identify one or more tissue engineering workflow components. For example, such parallel processing may entail analysing multiple wells of one or more multi-well plates imaged by a HTS or a high throughput flow cytometry (HTC) system.

For example, a method and a framework may be provided for modelling and automatic measurement of the essential physiological properties and parameters of cell cultures participating in the dynamic, morphogenesis-type phenomena. The method is based on simulations of the time dependent cell density (denoted by u(r, t)) by the Partial Differential Equations (PDE) techniques. The estimation of the physiological parameters of cells is conducted by applying a combination of optimization and interpolation techniques minimizing the discrepancy between experimentally measured cell density $u_{exp}(r, t)$ and its theoretical prediction $u_{theor}(r, t)$.

Various functions of aspects and embodiments of the invention may be implemented in software in the form of custom-designed modules, each representing specific assay geometry (e.g. "scratch assay") and physiology (e.g. "proliferation+chemotaxis"), and enabling concise quantification of physiology.

The final output delivered to a user may be a set of physiological parameters of cellular system (e.g. cells' proliferation index, diffusion coefficient, chemotactic sensitivity, death rate etc.), defined with the help of PDE modelling.

PDE formalism is widely applied to model physical, chemical and biological systems for both industrial and research purposes. A good example of the well elaborated PDE solver and applications is COMSOL framework.

In cellular assays applications, the Fisher equation (non-linear diffusion PDE) can be used to model the dynamics of cell density in cell proliferation/motility/invasion assays:

$$\frac{\partial u}{\partial t} = D_0 \nabla \cdot \left( \frac{A}{A + u/\bar{u}} \nabla u \right) + \alpha \cdot u(1 - u/\bar{u}) \qquad \text{Equation 1}$$

Equation 1 describes assay dynamics in terms of cell migration (diffusion coefficient $D_0$, contact inhibition A), and proliferation (mitotic index α, carrying capacity of the gel substrate $\bar{u}$) [7].

Fisher model's formulation (Equation 1) is naturally and concisely represented in terms of FlexPDE solver's script:
VARIABLES
u !cell density
DEFINITIONS
D0=21 !diffusion coefficient, [micron^2/min]
alpha=2.1*1e-3 !mitotic index, [1/min]
u_=1e-3 !limiting cell density,—"carrying capacity", [cells/micron^2]
A=0.1 !contact inhibition constant
EQUATIONS
u: dt(u)=D0*div(A/(A+u/u_))*grad(u))+alpha*u*(1−u/u_)

For other assay systems, when Fisher's model might insufficient or inadequate, a switch can be made to another, more appropriate PDE models.

For example, in order to introduce the chemotactic force into the Equation 1, one could use coupling of this equation with another equation describing the dynamics of chemoattractant (diffusion, decay, and secretion by cells). This approach might be considered as a specific case of the so-called Keller-Segel model:

$$\frac{\partial u}{\partial t} = D_0 \nabla \cdot \left( \frac{A}{A + u/\bar{u}} \nabla u \right) - \nabla \cdot [\chi(u, c) \nabla c] + \alpha \cdot u(1 - u/\bar{u}) \qquad \text{Equation 2}$$

$$\frac{\partial c}{\partial t} = D_c \nabla^2 c + \beta(u, c)u - \tau_c^{-1} c$$

where c(r, t) is chemoattractant density.

The corresponding representation of the model of Equation 2 in FlexPDE terms is as follows:
VARIABLES
u !cell density
c !chemoattractant density
DEFINITIONS
D0=21 !diffusion coefficient, [micron^2/min]
alpha=2.1*1e-3 !mitotic index, [1/min]
u_=1e-3 !limiting cell density,—"carrying capacity", [cells/micron^2]
A=0.1 !contact inhibition constant
!

D_C=600 !chemoattractant diffusion coefficient, [micron^2/min] (for VEGF)
tau_c=64 !chemoattractant decay time, [min]
beta_c=0.001 !rate of chemoattractant release, [mol/minute/micron^2]
chi_c=40 ! ? chemotactic sensitivity, [micron^2/min]
EQUATIONS
u: dt(u)=D0*div(A/(A+u/u_))*grad(u))+alpha*u*(1−u/u_)
c: dt(c)=D_c*div(grad(c))+beta_c*u−(1/tau_c)*c There exists an alternative PDE approach to cell motility exploiting the idea of fluid dynamics instead of diffusion (Gamba-Serini model). However, this model uses essentially the same equation for the concentration field of chemoattractant.

In general, PDE based methods allow to model intercellular effects, such as cell signalling, reaction-diffusion and decay of chemoattractants, cell-cell and cell-ECM interactions (traction, ECM digestion) and mechanical forces. Also, cellular processes as cell death, division, and cell sorting/differentiation are taken into account.

Therefore, relative contributions of these phenomena to the overall dynamics of cellular population(s) might be theoretically predicted.

The method might be considered as bridging technique, eventually aimed at modelling morphogenesis and organogenesis in more complicated objects such as engineered tissue constructs, cancer models (MTS), developmental systems, small animals, etc.

Figure 3:
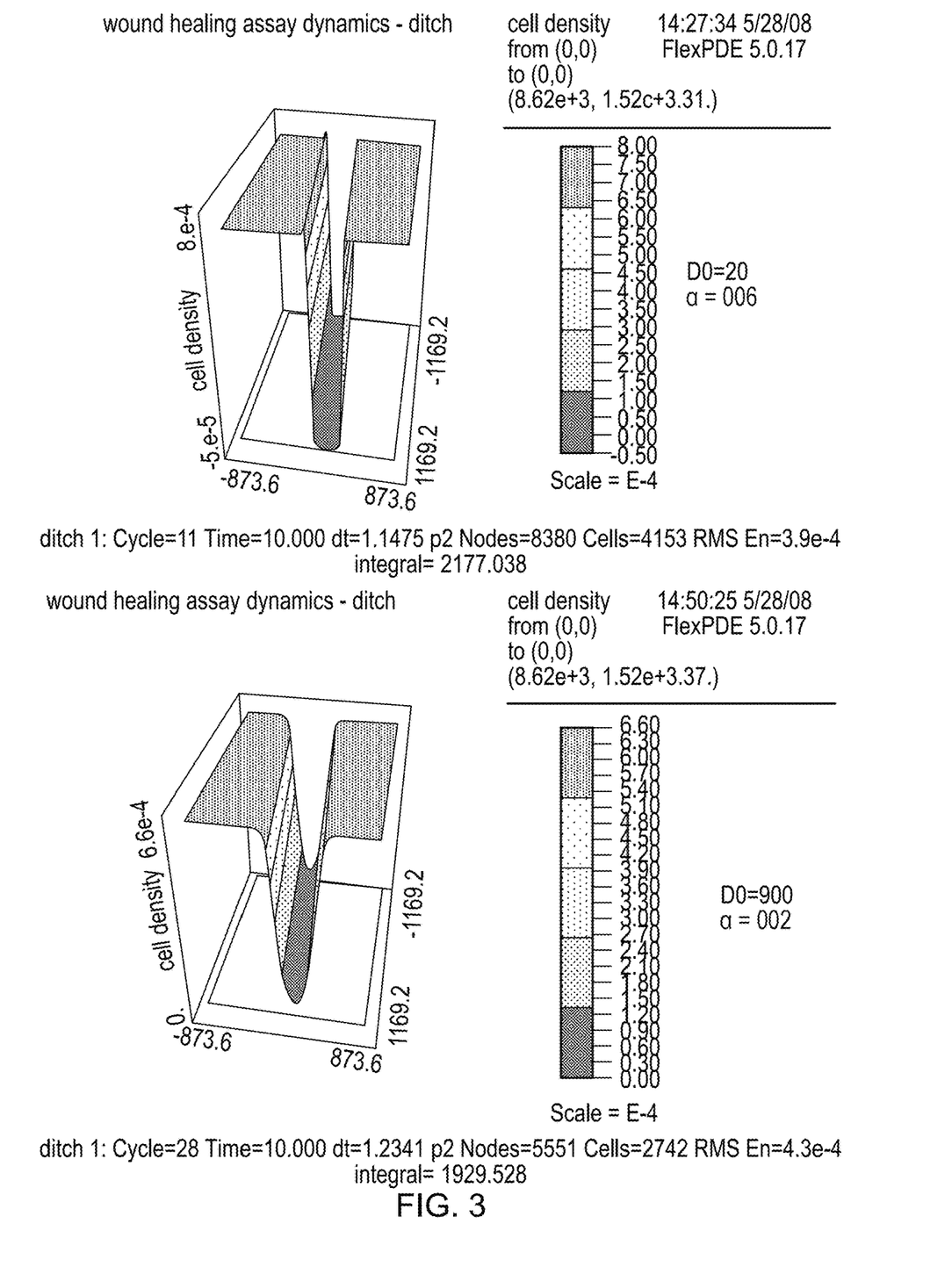
FIG. 3 shows modelling output for scratch assays simulating temporal evolution of wound healing in accordance with an embodiment of the present invention.

An example of modelling output is shown in FIG. 3. The example is represented by the temporal sequences of cell density u(r, t) simulated with the help of FlexPDE solver. The initial distribution of cell density was chosen to be characteristic for "wound healing", or "scratch" assay. In the upper figure D0=20 and α=0.06. In the lower figure D0=900 and α=0.02.

In the original model, the two "scratch" (upper and lower) figures provide animated movies that represent simulated temporal evolution of two wound healing assays with different motility/proliferation parameters. They show dynamics of assays over a 200 minute period, with the upper demonstrating gap closure dominated by cell proliferation and the lower gap closure dominated by cell motility.

Figure 4:
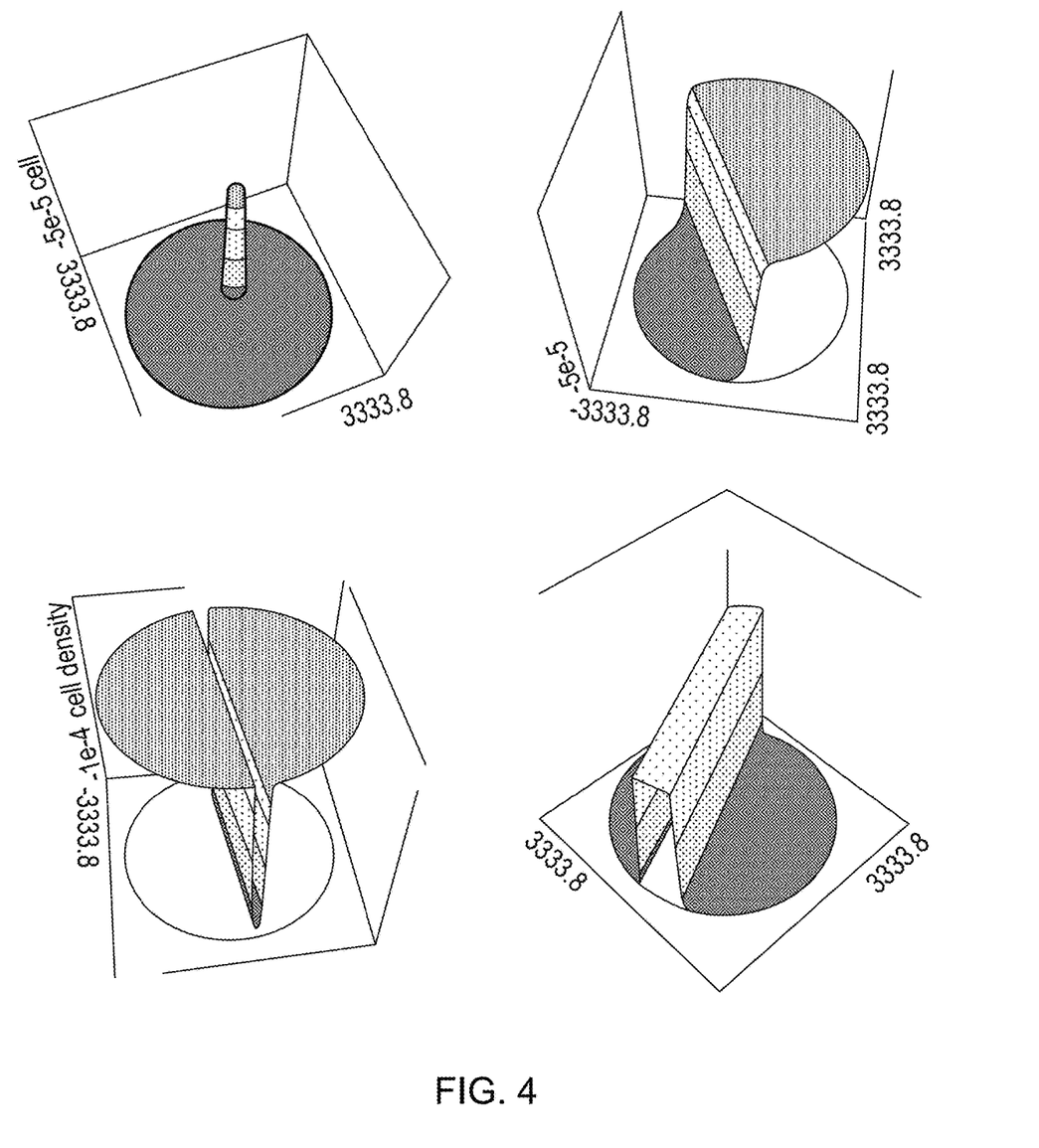
FIG. 4 shows different possible initial cell distributions for a model in accordance with various embodiments of the present invention.

Various experimental and biological techniques can be used to test the method, and FIG. 4 depicts examples of different possible initial cell density distributions that might, for example, be evaluated with the help of the PDE modelling approach in the well of a 96 well-plate.

The arrangement of the initial distribution of cell density u(r, t=0) is a non-trivial experimental procedure. Wound healing assays were prepared manually, by scratching the gel substrate, e.g. with a pipette tip.

One could possibly apply robotic spot printing technology to make initial cell density distributions in the shape of a localized spot, or set of spots.

Other automatic arrangements might be considered, since proposed method is able to work with different sample geometries, as shown in FIG. 4.

Also, the method is able to address the problem with uniform cell density distribution. This experiment can be used as "QA", or "initial gel calibration" to define the "carrying capacity", $\bar{u}$ of the gel substrate.

Figure 5:
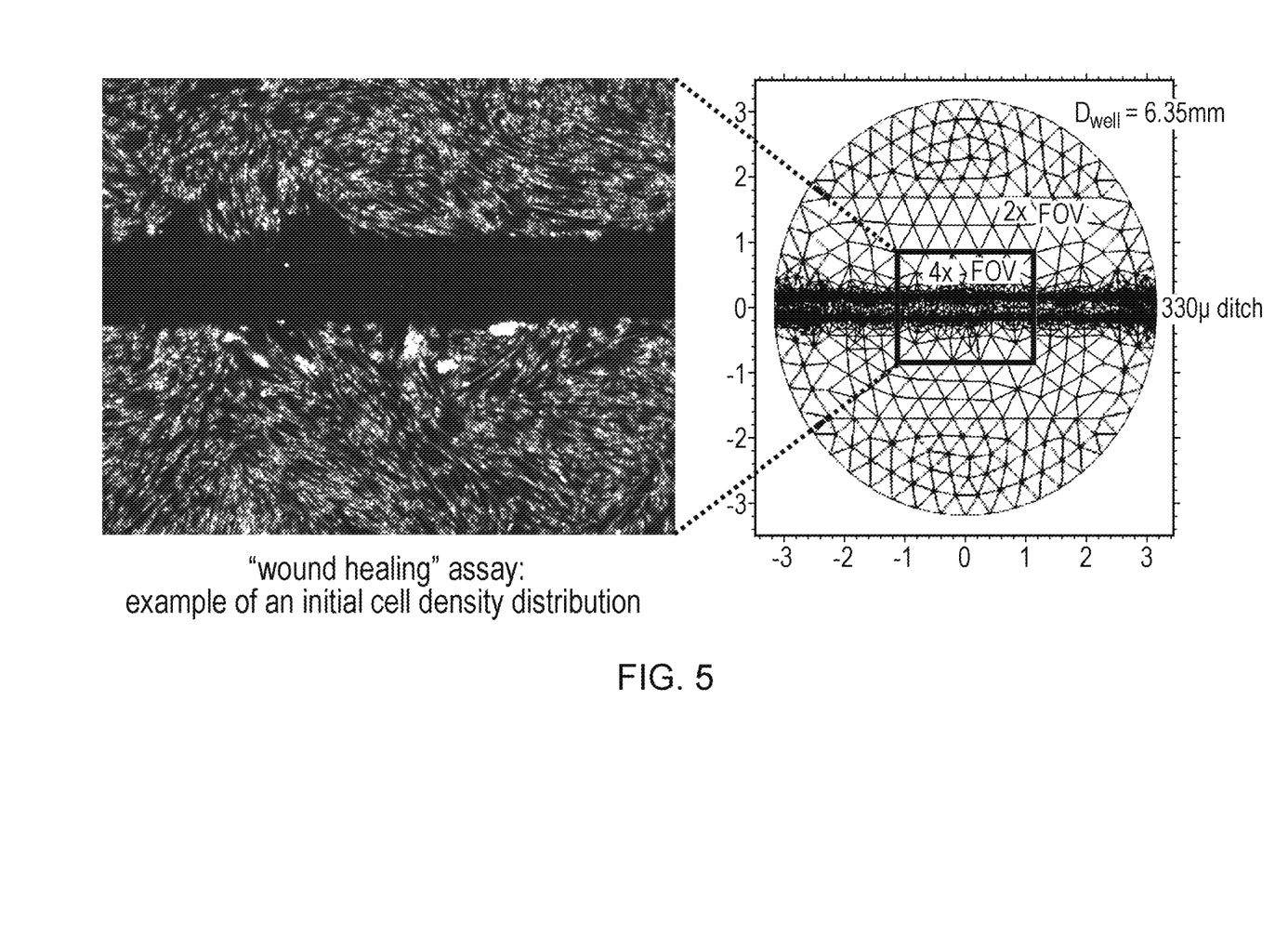
FIG. 5 shows a scratch arrangement of initial cell density for a wound healing assay in accordance with an embodiment of the present invention.

In order to analyse the sample, microscopy images were obtained using a GE IN Cell Analyzer system. From the microscopy and imaging viewpoint, low resolution biomicroscopy techniques are used for measuring cell density. Such a technique for a scratch arrangement of initial cell density is shown in FIG. 5. The images were obtained using a 2× objective. At 2×, cell nuclei are 2 to 4 pixels sized, and cells are 5 to 15 pixels sized, which is suitable for fast and high quality detection of cells by the available segmentation procedures (see below, for example).

Additional image processing methods can be used to compensate for irrelevant geometric effects (e.g. translation and rotation).

After defining positions of cells in the sample, the experimental cell density $u_{exp}(r, t)$ can be estimated by applying a procedure of the type described below.

Having obtained the experimental cell density data $u_{exp}(r, t)$, and corresponding modelled data $\underline{u}_{theor}(r, t)$, one can develop computational methods allowing estimation of model parameters. This step is non-trivial, since it can perform a search in the parameters space driven by the minimization of some data discrepancy functional that depends on many cell density functions, measured and modelled at different observation times.

A general method for parameters estimation, based on the overall "measurement vs theory" discrepancy functional, is described below. A proof of principle for this method, using a 1D example, is also presented below. This 1D example shows how the algorithms making parameter estimations based on experimental data and numeric modelled output (instead of theoretical expression), can be implemented.

Cell density estimation by Adjacency Graph (SOI, triangulation etc.)

The discrete estimate of cell density, calculated for the location (centre of gravity) rj of the detected cell (j-th cell), might be represented as an "effective number of cells divided by an effective area they occupy", in the form:

$$u_{exp}(r_j) \approx \frac{1 + n(\text{nghb\_AG}(j))/2}{\pi \cdot \bar{d}^2_{nghb\_AG(j)}} \text{ where} \qquad \text{Equation 3}$$

$$\bar{d}_{nghb\_AG(j)} = \frac{\sum_{\forall r_k \in \text{nghb\_AG}(j)} \|r_j - r_k\|}{n(\text{nghb\_AG}(j))} \qquad \text{Equation 4}$$

Figure 6:
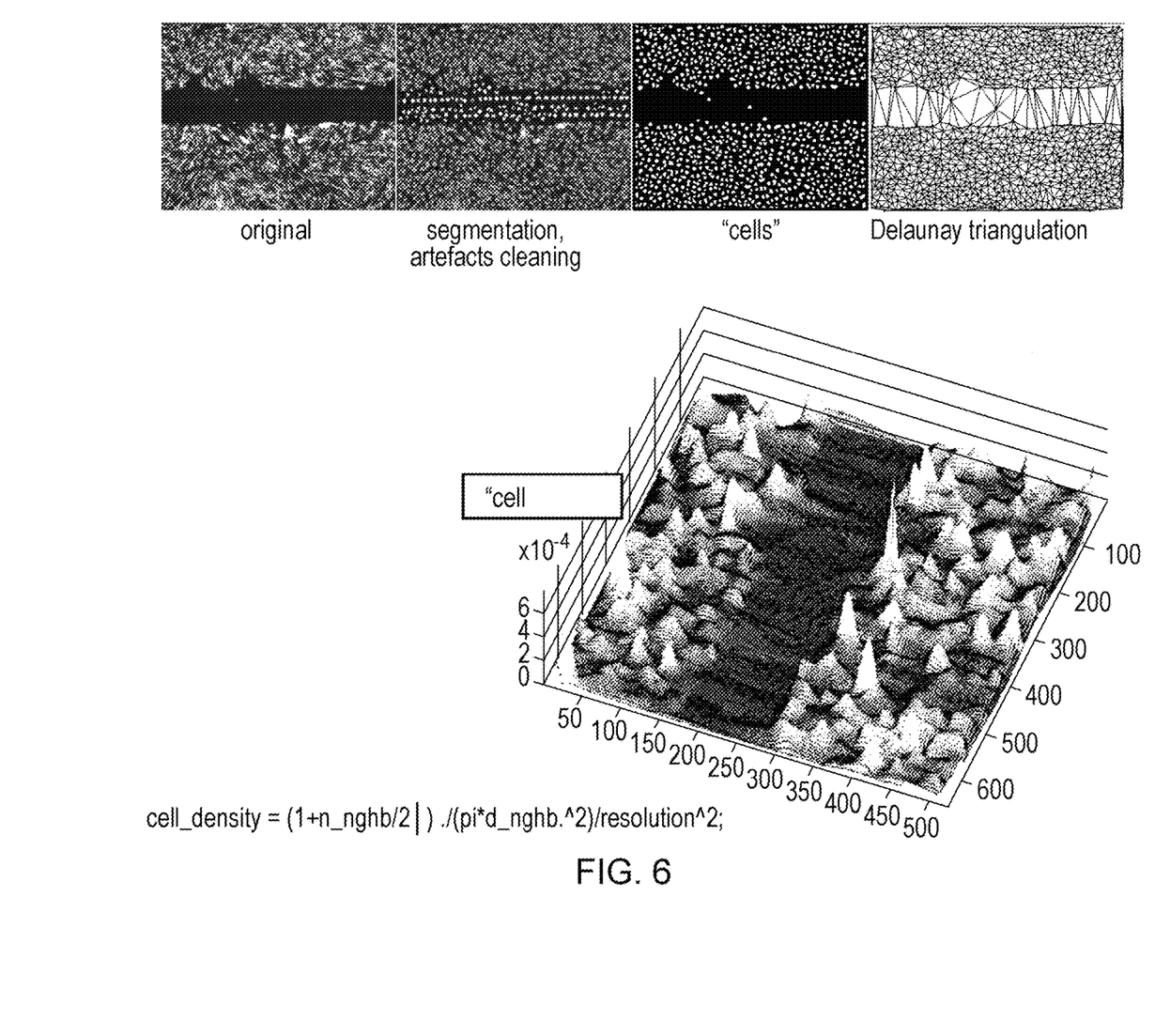
FIG. 6 shows an adjacency graph for use with various embodiments of the present invention.

In this formula, the symbol nghb_AG(j) denotes the set of points representing centres of gravity of cells classified as nearest neighbours of the cell under consideration (the j-th cell), in the cell-cell adjacency graph AG depicted in FIG. 6. The neighbours are the cells connected to the chosen cell by the edges of the AG graph of FIG. 6. FIG. 6 shows an example of an adjacency graph usage for peak sensitive segmentation (performed using GE Developer software) and Delaunay triangulation and data interpolation (performed using MATLAB).

The $\bar{d}_{nghb\_AG(j)}$ value given by Equation 4 is the mean distance from j-th cell to its AG-neighbour. Symbol n(A) is used to denote "the number of elements in A".

Experiment Vs. Simulated Data Comparison with Parameter Adjustment

The model outputs supplied by an ODE solver, for which analytical expressions aren't available, would need applying some techniques minimizing curves' mismatch functional. In particular, one of the options for computational comparison of theory with experiment is an adjustment of two curves, instead of fitting. Linear adjustment of the "theoretical" function $f(x)$ to the data y can be represented as:

$$\frac{y - y_0}{k_y} \sim f\left(\frac{x - x_0}{k_x}\right) \qquad \text{Equation 5}$$

where $y_0$, $k_y$, $x_0$, $k_x$ are the adjustment parameters. In this expression, argument transforms look less straightforward; however, it is quite easy to arrange two-parametric adjustment of the ordinate axis $y \sim y_0 + k_y \cdot f(x)$, in the case when arguments are fixed. Such an adjustment can be performed for equidistant as well as for non-equidistantly sampled data and should preferably involve the use of some sort of interpolation technique.

Figure 7:
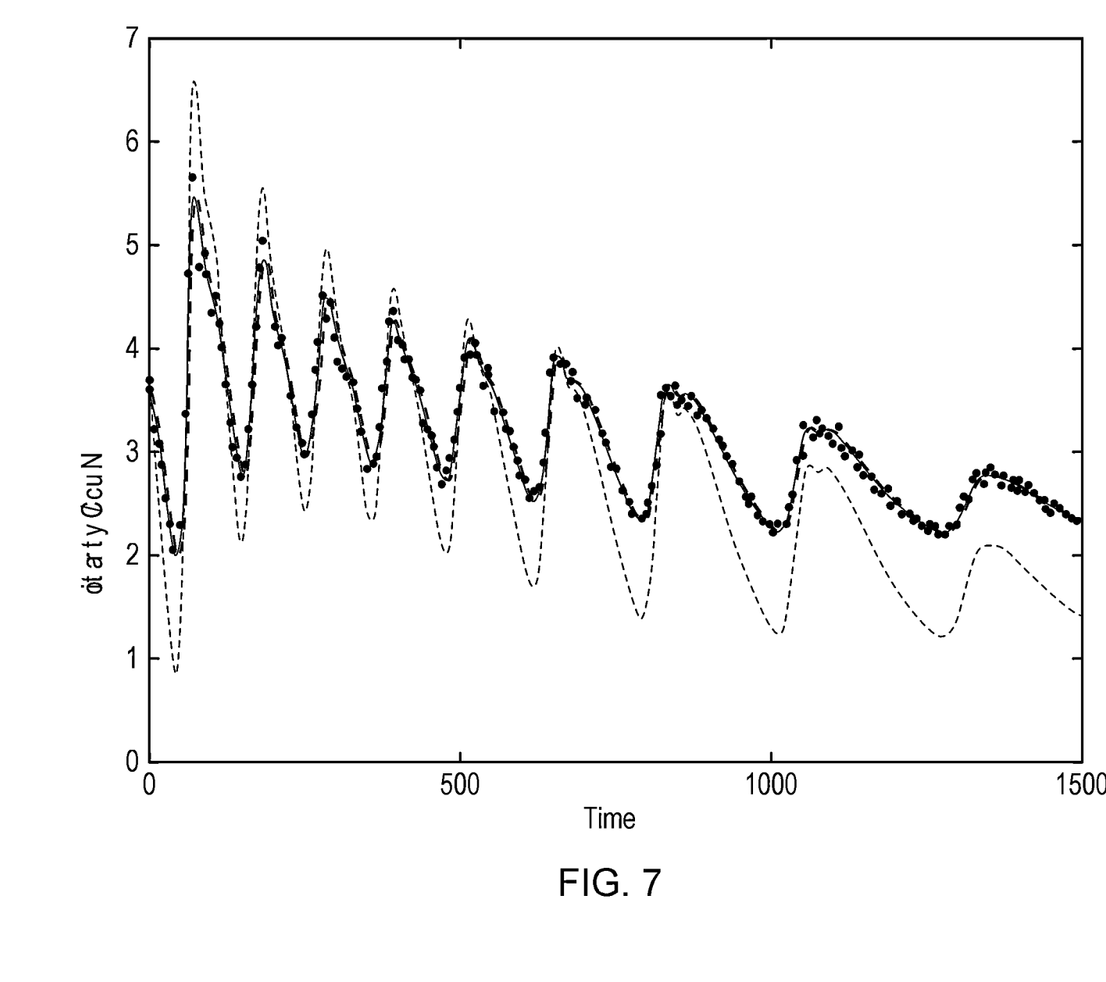
FIG. 7 shows a graph depicting comparison of experimental and theoretical data for automatic extraction of multi-cellular physiological parameters in accordance with various embodiments of the present invention.

This is illustrated in FIG. 7, which shows comparison of the "experimental" (point) and "theoretical" data (line) featured by y-axis adjustment. The resulting (adjusted) version of the "theoretical curve" is presented by a curve fitted to the experimental data points. No analytical expressions used, and the source curve (line) was calculated by combining the data based on fluorescent marker intensity and position related to NFκB (a transcription factor) concentration dynamics, obtained from a modified NFκB simulation. To simulate the experimental data, the source curve was sub-sampled, Y-stretched, Y-shifted, and noised. Y-axis shift and stretch parameters $y_0$ and $k_y$ were then fitted by the MATLAB function "fmins", by minimizing two-curve mismatch functional.

In general, the problem of estimation of model parameters might be approached in a way analogous to the above, by applying a procedure that minimizes the overall inter-field discrepancy functional. This functional, in its turn, depends on the choice of local vicinities used for interpolation of function values over corresponding grids.

The following denotations are introduced:

$G_U$ the grid used to define the discrete spatial function (discrete field) U. The $G_U$ is understood as a set of argument specifiers, e.g. XY nodes.

$n(G_U)$ number of elements in the set $G_U$ $g_U$ specific grid location in $G_U$: $g_U \in G_U$ $U(g_U)$ the value of the spatial function U defined at $g_U$ $\varepsilon_U(x)$ $G_U$-dependent spatial vicinity of the spatial point x (a set of nodes in $G_U$, located close to x. Certainly, $\varepsilon_U(x) \in G_U$, but in general $x \notin G_U$.

$U \circ \varepsilon_U(x)$ the value of spatial function U interpolated in the vicinity $\varepsilon_U(x)$, i.e. by using its natural grid $G_U$ locally. This technique is used to get the approximation of the value $U(x)$.

The discrepancy (error) between two spatial functions U and V might be calculated by choosing the grid $G_U$ as a base and performing local interpolation of the function V over its grid $G_V$:

$$E_{U \leftarrow V} = \frac{1}{n(G_U)} \sum_{\forall g_U \in G_U} [U(g_U) - V \cdot \varepsilon_V(g_U)]^2 \quad \text{Equation 6}$$

Analogously, the choice of the grid $G_V$ as a base will produce the estimate $E_{V \leftarrow U}$.

If there is no preference of the one grid over the other, one can use the half-sum estimate for the total discrepancy functional between two spatial functions U and V:

$$E_{U \div V} = E_{V \div U} = \frac{1}{2}(E_{U \leftarrow V} + E_{V \leftarrow U}) \quad \text{Equation 7}$$

By using the developed technique and denotations, the overall procedure of parameters estimate for the problem with temporal evolution is defined as following:

$$\vec{\alpha}^* = \text{argmin}_{\vec{\alpha}} \left[ \sum_m E_{u_{theor}(t_m, \vec{\alpha}) \div u_{exp}(t_m)} \right] \quad \text{Equation 8}$$

In Equation 8, the symbol $\vec{\alpha}^*$ denotes the resulting set of estimated parameters. The denotation $u_{theor}(t_m, \vec{\alpha})$ should be understood as "the theoretical (simulated) spatial function, calculated by a PDE solver for the time $t_m$ with the set of model parameters $\vec{\alpha}$"; here m is the index of the time point.

Correspondingly, the denotation $u_{exp}(t_m)$ is understood as "the spatial function measured at the time $t_m$ experimentally".

In the case when time sampling points $t_m$ are not the same for experimental and simulated data, one needs to complement this algorithm by an additional interpolation step or steps in time domain. That will need again considering arithmetic operations on two discrete fields defined, in general, on different grids. In this case, the technique utilized for deriving the expressions of Equations 6 and 7 can be reused.

Whilst the present invention has been described in relation to various embodiments, those skilled in the art will be aware that many other different embodiments of the present invention are possible with many varied applications.

For example, various embodiments may be adapted to apply various scheduling algorithms to control one or more robotic systems for growing tissue sample. A controller may be provided for automatically optimising tissue growth/morphogenesis, and such tissue may be multi-cellular, forming organs or components thereof. Certain embodiments may also include a cell concentrator or large-scale cell "incubator" for providing or growing the plurality of cells.

The cells for investigation may include pluripotent stem cells which can be embryonic or adult in origin, or have the ability to have pluripotency induced by addition of key growth factors and nutrient supplements. On the other hand, the cells may have possessed pluripotency capability at one stage of their life cycle, but instead have now been altered ("differentiated") into more specialised tissue cells, such as, but not limited to, those cells from heart, skin, bone, cartilage, liver and pancreas. Such differentiation of pluripotent cells has been described for certain cell and tissue types in the literature. However, it must be stressed that these methodologies are not universal for all cell types and standardisation is not a trivial exercise. Accordingly, the multi-cellular physiological parameters described herein would define one or more factors that are necessary to induce pluri-potency in the stem cells, as well as those factors that may control differentiation. For example, where the cells described may be adult stem cells, the multi-cellular physiological parameters will define those factors such as chemicals, conditions, steps, timing etc. that have statistically relevant influence to allow stem cells to develop from their pluri-potent state into a more differentiated tissue-specific phenotype.

In various embodiments, the controller may implement an adaptive learning algorithm that learns over time to enable optimised experimental morphogenesis testing and comparison to model predictions, and/or vice versa to validate models from measured data.

Various aspects permit 2D/3D mapping of cell migration, and/or 2D/3D mapping of specialised cell function, such as, for example, bone, vasculature, muscle formation, wound healing, etc. This may be implemented by upgrading an otherwise conventional high-throughput screening (HTS) apparatus, thereby enabling it to be adapted for studying and directing cell-cell and/or cell/ECM interactions. For example, various software, firmware and/or hardware upgrades may be made to add such functionality to IN Cell Analyzer 2000 system or a conventional Laboratory Information Management System (LIMS).

REFERENCES

2. CELLCULTURE Laboratory Information Management System
3. J. A. Thomson et al, "Embryonic Stem Cell Lines Derived from Human Blastocysts", Science, vol. 282, pp. 1145-1147, 6 Nov. 1998
4. K. Takahashi et al, "Induction of Pluripotent Stem Cells from Adult Human Fibroblasts by Defined Factors", Cell, vol. 131, pp. 861-872, 30 Nov. 2007
5. J. Yu et al, "Induced Pluripotent Stem Cell Lines Derived from Human Somatic Cells", Science, vol. 318, pp. 1917-1920, 21 Dec. 2007
6. G. Serini et al, "Modeling the Early Stages of Vascular Network Assembly", EMBO J., Vol. 22, No. 8, pp. 1771-1779, 15 Apr. 2003
7. Anna Q. Cai, Kerry A. Landman and Barry D. Hughes, "Multi-scale Modeling of a Wound Healing Cell Migration Assay", JTB 245, pp. 576-594, 2007

Where permitted, the content of the above-mentioned references are hereby also incorporated into this application by reference in their entirety.

The invention claimed is:

1. A system for automated extraction of multi-cellular physiological parameters to define a protocol of one or more sequentially applied steps necessary to grow a tissue sample, the system comprising:
   a morphogenesis module for growing a plurality of cells forming the tissue sample;
   a high-throughput screening microscope for monitoring the plurality of cells, wherein the high-throughput screening microscope is configured to:
      scan the plurality of cells; and
      generate data indicative of effects on cell growth of various combinations of the multi-cellular physiological parameters; and
   a controller for controlling the morphogenesis module and the high-throughput screening microscope to grow the plurality of cells and to analyze the growth of the plurality of cells, respectively, in order to determine the multi-cellular physiological parameters, wherein the controller comprises:
      a process modeling unit configured to:
         determine inter-cellular interactions in response to process conditions;
         generate one or more hypothetical protocols for growing the tissue sample, wherein the one or more hypothetical protocols are based at least in part on at least one of non-linear physics, self-organization, or morphogenesis theories; and
         send the one or more hypothetical protocols to a comparator unit for testing;
      a data mining unit configured to receive a first external theoretical hypothesis from an external computer system, the first external theoretical hypothesis comprising test protocol steps, wherein the first external theoretical hypothesis is distinguished from the one or more hypothetical protocols;
      a comparator unit in communication with the data mining unit and the process modeling unit, the comparator unit configured to:
         receive the one or more hypothetical protocols from the process modeling unit;
         receive actual tissue growth results from the monitoring unit;
         import the first external theoretical hypothesis from the data mining unit;
         perform a first testing of the one or more hypothetical protocols against the actual tissue growth results; and
         perform a second testing of the one or more hypothetical protocols against the first external theoretical hypothesis; and
      a control unit configured to:
         automatically and adaptively identify, based at least in part on the first and second testing performed by the comparator unit, the first external theoretical hypothesis, and the data provided by the monitoring unit, a most probable sequence of multi-cellular physiological parameters, and optimal sequential protocol steps and associated parameters in growing the tissue sample with a desired tissue type or structure thereof.

2. The system of claim 1, wherein the multi-cellular physiological parameters include one or more member selected from the group consisting of: pH, temperature, pressure, humidity, $O_2/CO_2$ levels, illumination levels, illumination wavelength, agents/reagents, ECM media, chemical signaling agents, physical and chemical conditions, morphogens, ligands, and drugs.

3. The system of claim 1, wherein the one or more hypothetical protocols for growing the tissue generated by the process modeling unit include one or more member selected from the group consisting of: symmetry breaking and topological instability, anisotropic aggregation, organ size conservation in polyploids, allometry, cell differentiation, cell proliferation, germ/soma separation in the course of evolution, wound healing, and embryo development.

4. The system of claim 1, wherein the morphogenesis module comprises an extra-cellular matrix (ECM) on which the plurality of cells is grown.

5. The system of claim 4, wherein the extra-cellular matrix (ECM) and the plurality of cells form the tissue sample.

6. The system of claim 4, further comprising a bio-printer for printing the cells layer by layer onto the ECM to build up the tissue sample.

* * * * *